United States Patent [19]

Graves

[11] Patent Number: 4,986,752
[45] Date of Patent: Jan. 22, 1991

[54] CUSHIONED CLAMP FOR SECURING A DENTAL DAM

[76] Inventor: R. Garry Graves, 945 Woodside Place, Victoria, British Columbia, Canada, V8Y 2P3

[21] Appl. No.: 134,214

[22] Filed: Dec. 16, 1987

[51] Int. Cl.$^5$ .............................................. A61C 5/12
[52] U.S. Cl. ..................................... 433/138; 433/139
[58] Field of Search ............... 433/139, 138, 137, 136, 433/140

[56] References Cited

U.S. PATENT DOCUMENTS

| | | | |
|---|---|---|---|
| 371,669 | 10/1887 | Carpenter | 433/138 |
| 562,490 | 6/1896 | Richter | 433/139 |
| 722,033 | 3/1903 | McCarter | 433/139 |
| 765,537 | 7/1904 | Abbott | 433/138 |
| 1,010,146 | 11/1911 | Ivory | 433/136 |
| 1,143,515 | 6/1915 | Dunlop | 433/139 |

Primary Examiner—John J. Wilson
Attorney, Agent, or Firm—Bull, Housser & Tupper

[57] ABSTRACT

A cushion for a dental rubber dam clamp has a body of an elastomeric material with a tooth engaging front face, a rear face and first and second ends. An elongated, slot-like recess communicates with the rear face and extends towards the front face from near the first end to near the second end. A method of securing a dental rubber dam clamp includes placing the cushion over at least one inside edge of the clamp and securing the clamp on a tooth so a portion of the cushion is compressed between the inside edge of the clamp and the tooth.

2 Claims, 2 Drawing Sheets

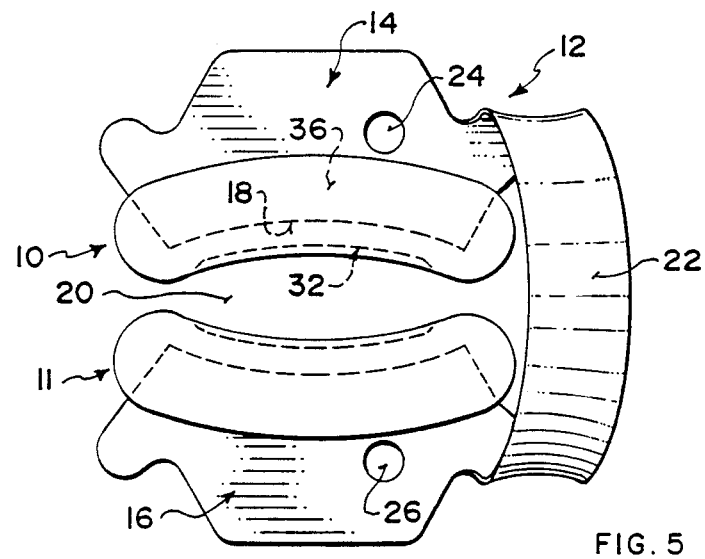
FIG. 5
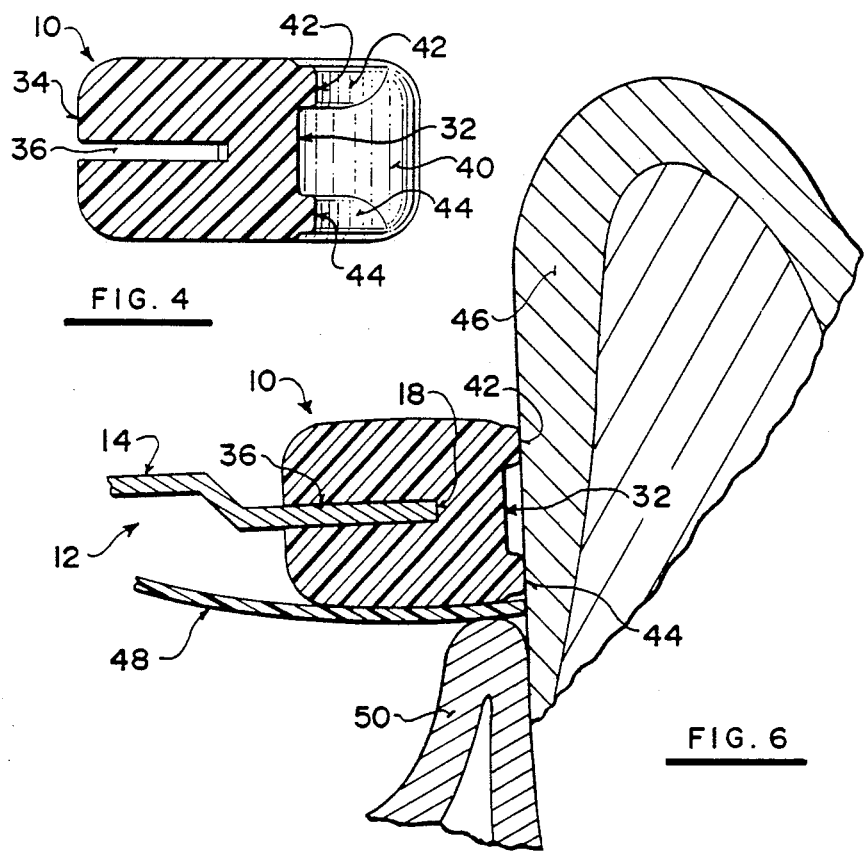
FIG. 4
FIG. 6

CUSHIONED CLAMP FOR SECURING A DENTAL DAM

BACKGROUND OF THE INVENTION

This invention relates to a cushion for a dental rubber dam clamp and a method of securing such a clamp.

It is conventional to isolate areas of the mouth of a dental patient from the throat during dental work such as drilling. This keeps the patient from ingesting material drilled from the tooth, water, filling material and other materials and chemicals utilized during dental treatment.

It is common to utilize resilient sheets, known as rubber dental dams, although they usually comprise synthetic materials rather than rubber. Openings are punched in the dam to receive those teeth which project through the openings. One or more spring metal dam clamps are used to engage selected teeth to hold the dam in place. These clamps are conventionally of spring metal, having two flat, thin jaw members with concave inside edges for engaging a tooth. A U-shaped spring bow portion interconnects the jaw portions and biases them towards each other. While these clamps are effective in holding the dam in position to protect the patient's gums, and prevent waste material and water from passing down the patient's throat, they can be uncomfortable. The hard metal of the jaws of the clamps can contact the patient's gums and the tooth root surface, causing pain. Sometimes a clamp slips during dental treatment, causing the patient to jump with the resulting pain. In addition, these clamps cannot be used on crowned teeth because they can damage the crowns. Consequently, there is a need to improve the comfort of dental rubber dam clamps, and a need to make them suitable for use on dental crowns.

U.S. Pat. No. 1,010,146 to Ivory discloses a pad holder for dental purposes. This device consists of means for holding an absorbent pad on a gum during a dental operation so as to absorb saliva at or about the tooth. The pad appears to be interposed between the tooth/gum area and jaws of the clamp, thus possibly protecting the tooth from the jaws to some extent. In some of the figures of the patent, however, the metal of the clamp appears to contact the teeth. The patent describes the pads fitted over the teeth and held firmly on the gum. Because the patent utilizes an absorbent pad, which is necessarily porous, it does not provide effective sealing. Moreover, the pads do not grip the clamp in such a manner as to be likely to prevent slipping.

U.S. Pat. No. 562,490 to Richter discloses a rubber dam clamp consisting of a flexible wire arrangement on metallic dental clamps employed to hold or retain absorbent wadding rolls. The metal of the clamp touches the tooth.

U.S. Pat. No. 722,033 to McCarter discloses a dental clamp in which the jaws of the clamp grip firmly the opposite sides of the tooth to be treated. It would appear that this device has the metal of the clamp in direct contact with the tooth.

SUMMARY OF THE INVENTION

The invention provides a cushion for a dental rubber dam clamp which includes a body of an elastomeric material, having a tooth-engaging front face, a rear face and first and second, opposite ends. An elongated, slot-like recess communicates with the rear face and extends towards the front face and from near said first end to near said second end.

The body may be curved so the front face is concave and the rear face is convex.

The body may have end portions adjacent the first and second ends extending from the front face to the rear face and between the recess and the first and second ends.

The front face may have a tooth engaging ridge extending from near the first end to near the second end of the body. Preferably there is a pair of spaced-apart, parallel ridges.

The invention also provides a combination of a dental rubber dam clamp and a cushion therefor.

The invention further provides a method of securing a dental rubber dam clamp. The method includes placing an elastomeric cushion over at least one inside edge of the clamp and securing the clamp on a tooth so the cushion is compressed between said at least one inside edge of the clamp and the tooth.

The invention provides distinct advantages for dental treatment. Firstly, patient comfort is significantly increased because a steel rubber dam clamp or other hard surface does not contact gingiva or cementum (the tooth root surface).

Sealing about the clamped tooth is improved, both to prevent leakage of saliva from below the rubber dam, and to prevent leakage of chemicals and other materials from above the rubber dam.

The dentist does not have to be concerned about the rubber dam clamp slipping further gingivally, and causing the patient to jump due to the clamp impinging on an anaesthetized gingiva or cementum. In certain situations, especially in the maxillary arch, the amount of anaesthetic used and the number of injections can be reduced.

If there is not a tooth immediately distal to the tooth being clamped, a matrix is easily placed on that tooth. Because of reduced pressure on the tooth from the jaw of the rubber dam clamp, the matrix band slips between the tooth and the rubber dam clamp fairly easily. It also facilitates easy removal of the matrix after placement of a restoration.

The need to clamp a tooth distal to a crown is negated. Instead, the crown tooth itself can be clamped without any damage to the crown.

The cushions can be used on one jaw or both jaws of the rubber dam clamp. This makes the cushions versatile. Furthermore, the cushions are easily cold sterilized, and are reusable several times. If a clamp does slip off a tooth, it does not tend to be propelled across the room as has occurred in the past without the use of cushions.

It should also be noted that the cushions according to the invention increase the conformity of the clamp with the shape of the tooth, and thus tend to provide improved retention of the clamp.

Minor disadvantages are encountered, although counterbalanced by the advantages outlined above. For one, the cushion cannot be used on teeth that have a low height of contour. Cushions cannot be used on teeth that have deep lingual or buccal extensions from the cavity preparation because they may be in the dental operator's way.

BRIEF DESCRIPTION OF THE DRAWINGS

In drawings which illustrate embodiments of the invention:

FIG. 4 is a sectional view taken along line 4—4 of FIG. 1;

FIG. 5 is a top plan of a combination of a rubber dam clamp with two cushions fitted thereto; and FIG. 6 is a transverse section through a portion of a tooth and gum in contact with a cushion according to the invention, and showing a fragment of a clamp jaw and a rubber dam associated therewith.

DESCRIPTION OF THE PREFERRED EMBODIMENTS

Figure 1:
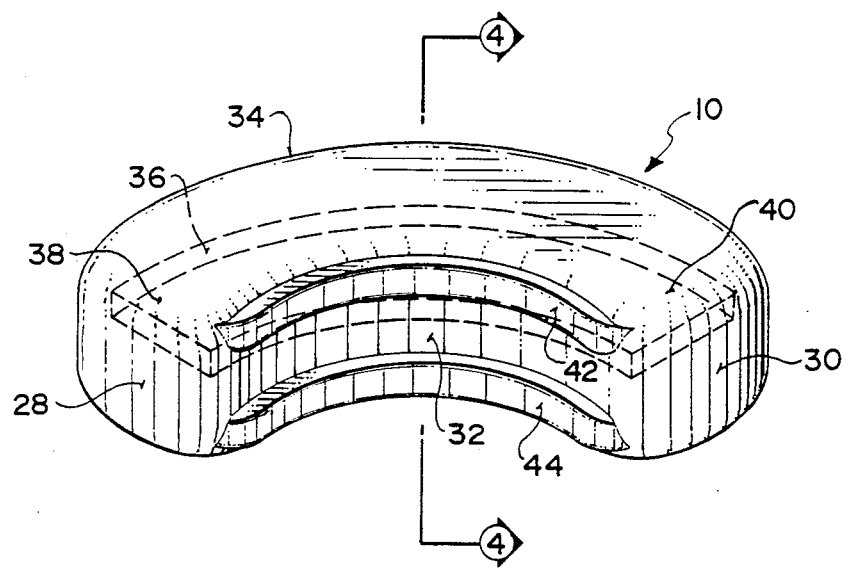
FIG. 1 is a perspective view of a cushion for a dental rubber dam clamp according to an embodiment of the invention.
Figure 2:
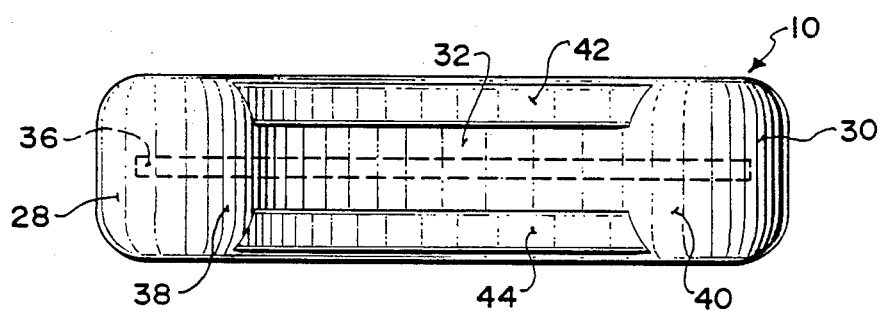
FIG. 2 is a front elevation thereof.

Referring to FIG. 5, this shows a cushion 10 for a dental rubber dam clamp 12, as well as an identical cushion 11. The clamp 12 is conventional, having a first jaw 14 and a second jaw 16. The jaws are thin and flat, and have concave inside edges, such as inside edge 18 of jaw 14 shown in broken lines. The inside edges are shaped to embrace a tooth placed within space 20 between the jaws.

A U-shaped spring bow portion 22 connects the jaws 14 and 16, and serves as a resilient member biasing the jaws towards each other. As may be observed, the jaws and member 22 are formed from a single piece of material, usually spring steel. There are apertures 24 and 26 in jaws 14 and 16 respectively. These are used to insert forceps to spread the jaws apart to facilitate placement of the clamp over a tooth. As described thus far, the clamp is conventional apart from the addition of cushions 10 and 11.

Since the cushions are identical, only cushion 10 will be described in detail. As seen in FIG. 1, cushion 10 is elongated from a first end 28 towards a second end 30. Front face 32 is concavely curved, while rear face 34 is convexly curved. Preferably the cushion is molded in this curved shape to facilitate placement on the clamp, although alternatively it could be straight and curved by forming it about the concave inside edge of the clamp, such as edge 18 shown in FIG. 5. An elastomeric material compatible with human tissue is employed and is non-porous in this preferred embodiment to enhance sealing against the tooth. The preferred material is an elastomeric thermo plastic sold by Shell Oil Co. and the Trade Mark KRETON because it it approved by the F.D.A. in the United States. Other natural or synthetic elastomeric can be used however.

Figure 3:
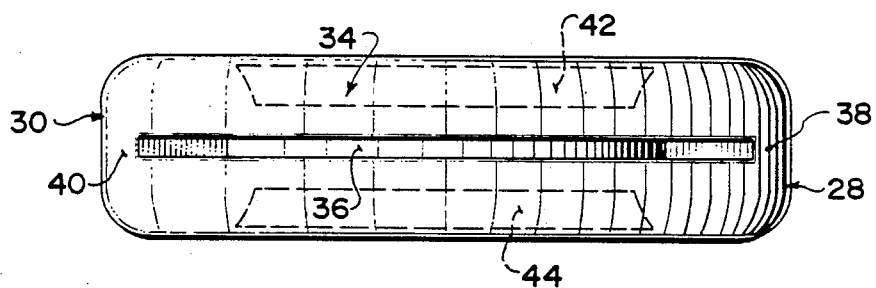
FIG. 3 is a rear elevation thereof.

A slot-like recess 36 extends inwardly from rear face 34 part way to front face 32 as shown best in FIGS. 3 and 4. This recess is elongated and straight and is shaped to tightly receive inside edge 18 of jaw 14 and seen best in FIG. 6.

The cushion has a first end portion 38 adjacent end 28, and a second end portion 40 adjacent end 30. These end portions extend from front face 32 to rear face 34 as may be seen in FIG. 1. Furthermore, the end portions extend from recess 36 to their respective end. For example, end portion 38 extends from the right end of slot 36, from the point of view of FIG. 3, to end 28 of the cushion. These end portions keep the cushion in place on the respective jaw of the clamp by preventing the jaw from sliding out the end of the slot, as might occur if slot 36 communicated with the ends. For this reason, the incorporation of end portions 38 and 40 is preferred structure though not essential.

As may be observed in FIG. 4, the cushion is substantially rectangular in section. Recess 36 extends from rear face 34 towards front face 32. The front face has means for sealingly gripping a tooth. This is in the form of a pair of spaced-apart parallel ridges 42 and 44. As may be seen in FIG. 4, these ridges are generally semi-cylindrical in section in this embodiment. The ridges are straight and extend from near one end 28 to the other end 30 of the cushion. As may be seen in FIG. 6, these ridges contact tooth 46 and provide sealing engagement. Although two parallel ridges are preferred as shown, one or more such ridges could be used alternatively. The clamp would work without these ridges, but its performance is enhanced by their inclusion.

Cushion 10 is used in a method of securing a dental rubber dam clamp as illustrated in FIG. 6. This shows a fragment of a conventional dental rubber dam 48, and of the conventional rubber dam clamp 12 described above and shown in better detail in FIG. 5. One or more of the cushions 10 and 11 is placed over one or both inside edges of the clamp, such as inside edge 18 shown in FIGS. 5 and 6. The clamp is then secured on a tooth, such as tooth 46 shown in FIG. 6, with the cushion 10 located between the clamp and the tooth, and the rubber dam 48 being between the cushion and the gum 50. The ridges 42 and 44 are shown in contact with the tooth to provide the sealing described above.

What is claimed is:

1. In combination:
  a dental rubber dam clamp having opposing jaw members with concave inside edges for engaging a tooth, said clamp having a resilient member interconnecting the jaw members and biasing the jaw members toward each other; and
  a cushion for at least one said jaw member fitted on said inside edge of said at least one jaw member, the cushion being elongated, and having a front face for engaging the tooth, a rear face, and a slot-like opening extending into said rear face towards the front face, the slot-like opening closely receiving said at least one jaw member, the front face having at least one elongated tooth engaging ridge extending therealong.

2. In combination:
  a dental rubber dam clamp having opposing jaw members with concave inside edges for engaging a tooth, said clamp having a resilient member interconnecting the jaw members and biasing the jaw members toward each other; and
  a cushion for at least one said jaw member fitted on said inside edge of said at least one jaw member, the cushion being elongated, and having a front face for engaging the tooth, a rear face, and a slot like opening extending into said rear face towards the front face the slot-like opening closely receiving said at least one jaw member, the front face having a pair of spaced apart parallel tooth engaging ridges extending therealong.

* * * * *